(12) United States Patent
Taneda et al.

(10) Patent No.: US 8,865,434 B2
(45) Date of Patent: Oct. 21, 2014

(54) METHOD OF PRODUCING SACCHARIDES CONTAINING GLUCOSE AS MAJOR CONSTITUENT

(75) Inventors: Daisuke Taneda, Hitachinaka (JP); Makoto Ikeo, Mito (JP)

(73) Assignee: JGC Corporation, Tokyo (JP)

( * ) Notice: Subject to any disclaimer, the term of this patent is extended or adjusted under 35 U.S.C. 154(b) by 0 days.

(21) Appl. No.: 13/335,697

(22) Filed: Dec. 22, 2011

(65) Prior Publication Data

US 2012/0164694 A1 Jun. 28, 2012

(30) Foreign Application Priority Data

Dec. 28, 2010 (JP) ................................. 2010-293275

(51) Int. Cl.
C12P 19/14 (2006.01)

(52) U.S. Cl.
CPC ..................................... C12P 19/14 (2013.01)
USPC .......................................................... 435/99

(58) Field of Classification Search
USPC .......................................................... 435/99
See application file for complete search history.

(56) References Cited

U.S. PATENT DOCUMENTS

| 5,733,758 A * | 3/1998 | Nguyen ........................ 435/162 |
| 2008/0138862 A1* | 6/2008 | Felby et al. ..................... 435/72 |
| 2009/0035826 A1* | 2/2009 | Tolan et al. ..................... 435/99 |
| 2009/0053777 A1* | 2/2009 | Hennessey et al. ............ 435/101 |

FOREIGN PATENT DOCUMENTS

| JP | H01-277482 | 11/1989 |
| WO | WO 2011/074479 A1 | 6/2011 |

OTHER PUBLICATIONS

Prasetyo et al., Appl. Biochem. Biotechnol. 162: 52-61 (2010).*
International Search Report in application No. PCT/JP2010/072153 mailed on Feb. 15, 2011 in 4 pages.
W. Sattler, H. Esterbauer, O. Glatter, W. Steiner, "The Effect of Enzyme Concentration on the Rate of the Hydrolysis of Cellulose", Biotechnology and Bioengineering, vol. 33, pp. 1221-1234 (1989).
Yanpin Lu, Bin Yang, David Gregg, John N. Saddler, and Shawn D. Mansfield, "Cellulase Adsorption and an Evaluation of Enzyme Recycle During Hydrolysis of Steam-Exploded Softwood Residues", Applied Biochemistry and Biotechnology, vols. 98-100, pp. 641-654, 2002.
Farzaneh Teymouri, Lizbeth Laureano-Perez, Hasan Alizadeh, Bruce E. Dale, "Optimization of the ammonia fiber explosion (AFEX) treatment parameters for enzymatic hydrolysis of corn stover", Bioresource Technology 96, pp. 2014-2018, 2005.
Ming Chen, Liming Xia, Peijian Xue, "Enzymatic hydrolysis of corncob and ethanol production from cellulosic hydrolysate", International Biodeterioration & Biodegradation 59 (2007) 85-89.

(Continued)

*Primary Examiner* — Patricia A Leith
*Assistant Examiner* — Erin M Bowers
(74) *Attorney, Agent, or Firm* — Knobbe Martens Olson & Bear LLP

(57) ABSTRACT

A method of producing saccharides containing glucose as the major constituent by degrading at least one selected from the group consisting of cellulose and hemicellulose with a cellulose saccharifying enzyme is provided. The method includes the steps of: mixing a cellulose material and a solution containing cellulose saccharifying enzyme to prepare a mixture; and saccharifying the cellulose material with the saccharifying enzyme. A gross energy density Y (W/m$^3$) subjected to the mixture and a substrate concentration X (w/v%) of the cellulose material to the enzyme solution satisfy a formula (1) below during the step of saccharifying.

$$Y \leq -0.0125X^2 + 1.195X + 23.25 \qquad (1)$$

2 Claims, 2 Drawing Sheets

(56) References Cited

OTHER PUBLICATIONS

M. Sakata, H. Ooshima, Y. Harano, "Effects of Agitation on Enzymatic Saccharification of Cellulose", Biotechnology Letters, vol. 7, No. 9, pp. 689-694 (1985).

Hanna Ingesson, Guido Zacchi, Bin Yang, Ali R. Esteghlalian, John N. Saddler, "The effect of shaking regime on the rate and extent of enzymatic hydrolysis of cellulose", Journal of Biotechnology 88, pp. 177-182 (2001).

Henning Jørgensen, Jakob Vibe-Pedersen, Jan Larsen, Claus Felby, "Liquefaction of Lignocellulose at High-Solids Concentrations", Biotechnology and Bioengineering, vol. 96, No. 5, pp. 862-870, Apr. 1, 2007.

Masashi Sakurai, Yasuyuki Takahata, and Koji Takahasi, "Stirring Operation in Saccharification of Cellulosic Biomass", Chemical Engineering, Mar. 2009, pp. 68-72.

K. Karim, et al., "Anaerobic Digestion of Animal Waste: Waste Strength Versus Impact of Mixing", Bioresource Technology, vol. 96, 2003, pp. 1771-1781.

S.R. Lamping, et al., "The Design of a Prototype Miniature Bioreactor for High Throughput Automated Bioprocessing", Chemical Engineering Science, vol. 58, 2003, pp. 747-758.

J. A. Sánchez Pérez, et al., "Shear Rate in Stirred Tank and Bubble Column Bioreactors", Chemical Engineering Journal, vol. 124, 2006, pp. 1-5.

Tadashi Takahashi, "Researches Into Development of New Material From Apple Juice Extraction Residue with Microorganisms (Part 1)," Report of Aomori Industrial Research Institute Report, Aomori Industrial Research Institute, Sep. 2001, vol. 2000, pp. 94-105.

Daisuke Taneda et al., "Preparing High-Concentration Carbohydrate Solution by Enzymatic Saccharification," Abstracts of $41^{st}$ Autumn Meeting of the Society of Chemical Engineers, Japan, Aug. 2009, p. 146.

Yoshiki Ueno et al., "Study of Enzymatic Saccharification Reaction Device," Abstract of $41^{st}$ Autumn Meeting of the Society of Chemical Engineers, Japan, Aug. 2009, p. 147.

\* cited by examiner

METHOD OF PRODUCING SACCHARIDES CONTAINING GLUCOSE AS MAJOR CONSTITUENT

BACKGROUND OF THE INVENTION

1. Field of the Invention

The present invention relates to a method of producing saccharides containing glucose as the major constituent by an enzymatic saccharification in which cellulose or hemicellulose in a biomass is enzymatically degraded. Particularly, the present invention relates to a method of producing saccharides containing glucose as the major constituent capable of increasing glucose production by an efficient enzymatic saccharification with a small amount of enzyme.

Priority is claimed on Japanese Patent Application No. 2010-293275, filed Dec. 28, 2010, the content of which is incorporated herein by reference.

2. Description of Related Art

Nowadays, research and development of techniques for producing bioethanol from a cellulosic biomass are conducted all over the world. Woods, grasses, residuals of agricultural products, used papers, paper sludges, cotton fibers, or the like, are examples of the cellulosic biomass. More specifically, construction waste, wood wastes, straws, bagasse (the fibrous matter that remains after sugarcane or sorghum stalks are crushed), corn stover, or the like can be named as examples of the cellulosic biomass.

The concentrated and diluted sulfuric acid methods, and the enzymatic method have been developed as methods of producing bioethanol, in which saccharides produced from the cellulosic biomass are fermented to produce ethanol. In recent years, the enzymatic method has drawn particular attention.

In the enzymatic method, cellulose and hemicellulose in the biomass are degraded with an enzyme to produce saccharides. Then, the produced saccharides are fermented to ethanol by fermenting microorganisms, such as yeast.

Cellulose is a simple polysaccharide that is formed by dehydration condensation of glucose. Thus, when the cellulose is hydrolyzed (enzymatic degradation), glucose is produced.

Hemicellulose is a complex polysaccharide that is formed by dehydration condensation of glucose, xylose, mannose, and the like. Thus, when the hemicellulose is hydrolyzed (enzymatic degradation), glucose, xylose, mannose and the like are produced.

A fermentating microorganism is added to a solution containing saccharides obtained by the enzymatic saccharification using cellulose and hemicellulose. Then ethanol is produced by fermentation of the saccharides.

In the conventional enzymatic saccharification of cellulose and hemicellulose, a biomass containing cellulose and/or hemicellulose and a solution containing an enzyme (enzyme solution) are mixed to prepare a mixed solution (slurry). Then, an enzymatic saccharification of the cellulose and/or hemicellulose is performed in a condition where the mixed solution is stirred or shaken. It has been reported that the lower the amount of enzyme used, the lower the amount of sugar produced in the conventional enzymatic saccharification of cellulose and hemicellulose.(see Non-Patent Literature 1: W. Sattler, H. Esterbauer, O. Glatter, W. Steiner, "The Effect of Enzyme Concentration on the Rate of the Hydrolysis of Cellulose" Biotechnology and Bioengineering, Vol. 33, pp. 1221-1234 (1989); Non-Patent Literature 2: Yanpin Lu, Bin Yang, David Gregg, John N. Saddler, Shawn D. Mansfield, "Cellulase Adsorption and an Evalution of Enzyme Recycle During Hydrolysis of Steam-Exploded Softwood Residues" Applied Biochemistry and Biotechnology, Vols. 98-100, 2002; Non-Patent Literature 3: Farzaneh Teymouri, Lizbeth Laureano-Perez, Hasan Alizadeh, Bruce E. Dale, "Optimization of the ammonia fiber explosion (AFEX) treatment parameters for enzymatic hydrolysis of corn stover" Bioresource Technology 96, pp. 2014-2018, 2005; Non-Patent Literature 4: Ming Chen, Liming Xia, Peijian Xue, "Enzymatic hydrolysis of corncob and ethanol production from cellulosic hydrolysate" International Biodeterioration & Biodegradation 59 (2007) 85-89).

It is very critical to reduce the amount of the saccharifying enzyme to put the enzymatic saccharification process into practical use, since the saccharifying enzyme is expensive. However, the problem of lowered sugar production associated with reduced enzyme loading has been preventing the reduction of the enzyme loading. However, the reason causing the problem has not been understood, and a way to solve the problem has not been established. Therefore, research and development has been focused mainly on 1) increasing enzymatic activity of the saccharifying enzyme and 2) increasing efficiency of the saccharifying enzyme by modifying the structure of biomass, such as the crystal structures of cellulose.

It has been found that the amount of the saccharifying enzyme can be reduced without a significant ratio of the enzyme being deactivated by optimizing the reaction condition of the biomass including the saccharifying enzyme and cellulose and/or hemicellulose (Patent Literature 1: WO 2011/074479). As explained above, in the conventional method, the enzymatic degrading reaction, in which cellulose and/or hemicellulose are reacted with the saccharifying enzyme, is performed under the condition where the mixed solution is stirred or shaken. Contrary to that, in the method describe in Patent Literature 1, the enzymatic saccharification is performed under a condition where the mixed solution is undisturbed without stirring and shaking. In the method, the mixing solution is undisturbed, or only subjected to intermittent stirring or shaking. In the method described in Patent Literature 1, the amount of the saccharifying enzyme can be reduced without a significant ratio of the enzyme being deactivated.

The reason why the amount of the saccharifying enzyme can be reduced without a significant ratio of the enzyme being deactivated when the mixed solution is not stirred or shaken is explained below.

Conventionally, it has been believed that reaction rate of the enzymatic degradation is improved when the mixed solution is stirred or shaken, since temperature and ingredients of the solution are more evenly distributed in the reaction tank. Therefore, in the conventional enzymatic saccharification, the enzymatic saccharification is performed by stirring the mixed solution (slurry), after preparing the mixed solution (slurry) by mixing a biomass containing cellulose and/or hemicellulose and a solution containing a saccharifying enzyme (enzyme solution). As a result, there are many reports describing case studies investigating a slurry stirring condition and a slurry stirring apparatus. For example, effects of 1) speed of stirring, 2) shape of stirring impeller, 3) structure stirring apparatus, and the like are investigated (see Non-Patent Literature 5: M. Sakata, H. Ooshima, Y Harano, "EFFECTS OF AGITATION ON ENZYMATIC SACCHARIFICATION OF CELLULOSE" Biotechnology Letters, Vol.7, No. 9, pp. 689-694 (1985); Non-Patent Literature 6: Hanna Ingesson, Guido Zacchi, Bin Yang, Ali R. Esteghlalian, John N. Saddler, "The effect of shaking regime on the rate and extent of enzymatic hydrolysis of cellulose" Journal of Biotechnology 88, pp. 177-182 (2001); Non-Patent Literature 7: Henning Jorgensen, Jakob Vibe-Pedersen, Jan Larsen, Claus Felby, "Liquefaction of Lignocellulose at High-Solids Concentrations" Biotechnology and Bioengineering, Vol. 96, No. 5, pp. 862-870, Apr. 1, 2007; and Non-Patent Literature 8: M. Sakurai, Y Takahata, K. Takahashi, "Stirring Operation in Enzymatic Saccharification of Cellulosic Biomass" Chemical Engineering, pp. 68-72, March (2009)).

However, the effect of enzyme concentration has not been paid attention in these reports. It has been known that the saccharifying enzyme, which hydrolyzes cellulose and/or hemicellulose into monosaccharide, is deactivated when it is subjected to a high physical stress due to stirring, shaking, or the like. However, it has not been known that extent of the enzyme deactivation can vary extremely depending on the concentration of the saccharifying enzyme. Here, the inventors found that when the enzyme concentration is high, the deactivation rate of the saccharifying enzyme can be reduced even if the enzyme solution is subjected to a physical stress. Also, when the enzyme concentration is low, deactivation rate of the saccharifying enzyme was extremely high in case where the enzyme solution is subjected to the same physical stress (see FIG. 4).

With an experimental data showing rate of enzyme deactivation is low in a condition where the concentration of the saccharifying enzyme is high, the stirring process has been performed in a condition where the concentration of the enzyme is low in the conventional methods, since the enzyme concentration effect to the physical tolerance of the enzyme has not been known. That leads to a significant deactivation of the enzyme occurs, making it difficult to reduce the amount of the enzyme. In the present specification, deactivation means that an enzyme having a hydrolyzing activity loses the activity. More specifically, it means an enzyme having an activity to hydrolyze cellulose and/or hemicellulose into a monosaccharide loses the activity.

The phenomenon described above is explained using FIG. 4. FIG. 4. is a graph showing a relationship between reaction time (x-axis) and amount of enzyme deactivation (y-axis) during incubation.

In the reaction, four 100 mL-volume enzyme solutions were prepared by dissolving an enzyme to 100 ml of 50 mM acetate buffer, pH of which is adjusted to 5. Enzyme concentration of the first and second enzyme solutions were 0.6 g/L and that of the third and fourth enzyme solutions were 6 g/L. Then, the four enzyme solutions were incubated at 50° C. for indicated period. During the incubation, the first and third enzyme solutions were subjected to stirring density of 73 W/m$^3$, while the second and fourth enzyme solutions were allowed to stand without stirring. Samples were taken from the enzyme solutions in multiple incubation time points and the rate of enzyme deactivation was monitored and plotted in the graph shown in FIG. 4.

As shown in FIG. 4, extent of enzyme deactivation was significantly higher when the enzyme concentration was 0.6 g/L (see open triangle symbols) compared to the case where the concentration was 6 g/L (see open circle symbols). Also, it was demonstrated that the rate of enzyme deactivation was higher when the solutions were stirred compared to the cases in which the solutions were allowed to stand (compare open and solid circles, or open and solid triangles).

In previous researches and developments investigating speed of stirring and a structure of stirring apparatus, experiments have been performed in a condition where the concentration of the saccharifying enzyme is high. Therefore, they have been performed in a condition in which the rate of enzyme deactivation due to a physical stress, such as stirring, is inherently low. When the concentration of the saccharifying enzyme is reduced to decrease the amount of the enzyme used, the enzyme is deactivated at an even higher degree. Accordingly, the lower the enzyme concentration, the higher the rate of the enzyme deactivation.

Because of reasons described above, the rate of enzyme deactivation becomes higher under a condition where the concentration of the enzyme is low and the mixed solution is stirred or shaken, reducing the degradation rate of cellulose and/or hemicellulose. Because of the lack of knowledge of the enzyme deactivating effect under the condition where the enzyme concentration is low and the mixed solution is subjected to physical stress, reducing the amount of the saccharifying enzyme used without a significant ratio of the enzyme being deactivated has been practically impossible.

To solve the problem described above, in the method described in Patent Literature 1, the enzymatic reaction is proceeded in a condition where the mixed solution is allowed to stand without stirring or shaking, contrary to the conventional methods, in which the mixed solution is stirred or shaken. By adopting the method described in Patent Literature 1, the amount of enzyme used has been reduced.

An disadvantage of the method described in Patent Literature 1 is that obtaining evenly distributed temperature and ingredients in the mixed solution becomes difficult without stirring or shaking when the reaction apparatus is scaled up in practical use. In short, the method described in Patent Literature 1 has an advantage and disadvantage. The advantage is that the rate of enzyme deactivation is lowered even if the concentration of the enzyme was low. The disadvantage is that the enzymatic reaction proceeds inefficiently because of the unevenly distributed temperature and ingredient in the mixed solution.

SUMMARY OF THE INVENTION

Problems to be Solved by the Invention

As explained above, establishing a method to increase the amount of sugar production using less of the saccharifying enzyme is needed, since the enzymes used in the enzymatic saccharification are expensive. However, when the mixed solution (slurry) including a cellulosic biomass is subjected to stirring or shaking in conventional methods, lowering the enzyme concentration causes increased rate of enzyme deactivation. Therefore, it was impossible to obtain effective enzymatic degradation of biomass with a small amount of the saccharifying enzyme.

The present invention has been made under the circumstances described above. The purpose of the present invention is to provide a method of producing saccharides containing glucose as the major constituent. In the method of producing saccharides of the present invention, production of saccharides containing glucose as the major constituent can be increased even if the enzymatic saccharification is performed with a small amount of the enzyme.

Means for Solving the Problem

An aspect of the present invention is a method of producing saccharides containing glucose as the major constituent (hereinafter referred as "the method of producing saccharides of the present invention") by degrading at least one selected from the group consisting of cellulose and hemicellulose with a cellulose saccharifying enzyme, comprising the steps of: mixing the at least one selected from the group consisting of cellulose and hemicellulose with an enzyme solution containing a cellulose saccharifying enzyme to prepare a mixture; and saccharifying the at least one selected from the group consisting of cellulose and hemicellulose with the cellulose saccharifying enzyme after the step of mixing in a reaction tank, wherein, an energy density Y (W/m$^3$) subjected to the mixture and a substrate concentration X (w/v %) of the at least one selected from the group consisting of cellulose and hemicellulose to the enzyme solution satisfy a formula (1) below during the step of saccharifying.

$$Y \leq -0.0125X^2 + 1.195X + 23.25 \qquad (1)$$

In the method of producing saccharides of the present invention, at least one selected from the group consisting of cellulose and hemicellulose may be a biomass that is pretreated.

Effects of the Invention

A biomass substrate, which is introduced into the enzymatic saccharification, contains insoluble solid materials. Therefore, the total force subjected to the mixture (gross force) is reduced by a certain degree (net force) depending on a substrate concentration (ratio of the substrate added to the enzyme solution) of the biomass substrate to the mixture.

In the method of producing saccharides of the present invention, the energy density subjected to the mixture (gross force) and the substrate concentration of a biomass substrate to the mixture are controlled based on the formula (1) below to adjust the real force subjected on the enzymes.

$$Y \leq -0.0125X^2 + 1.195X + 23.25 \qquad (1)$$

As a result, deterioration of the enzyme (deactivation of the enzyme) can be suppressed in the mixture even if the mixture is mixed vigorously. Consequently, the production of saccharides containing glucose as the major constituent can be increased even if the enzymatic saccharification is performed with a small amount of the enzyme.

DETAILED DESCRIPTION OF THE INVENTION

Embodiments of the Invention

Figure 1:
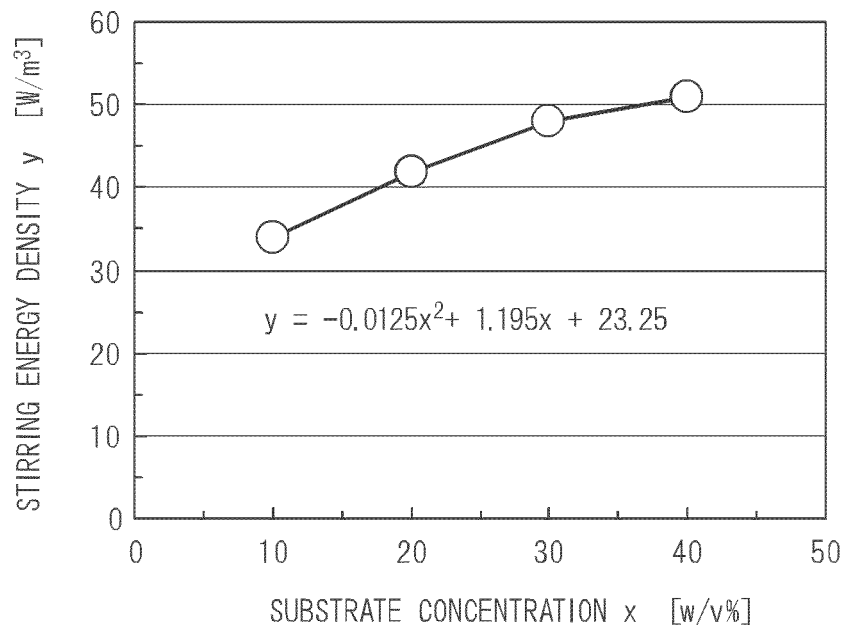
FIG. 1 is a graph showing a relationship between the substrate concentration in the enzyme solution (w/v %) and the maximum gross stirring energy density (W/m$^3$) that can be subjected to the mixture without causing a significant enzyme deactivation.
Figure 2:
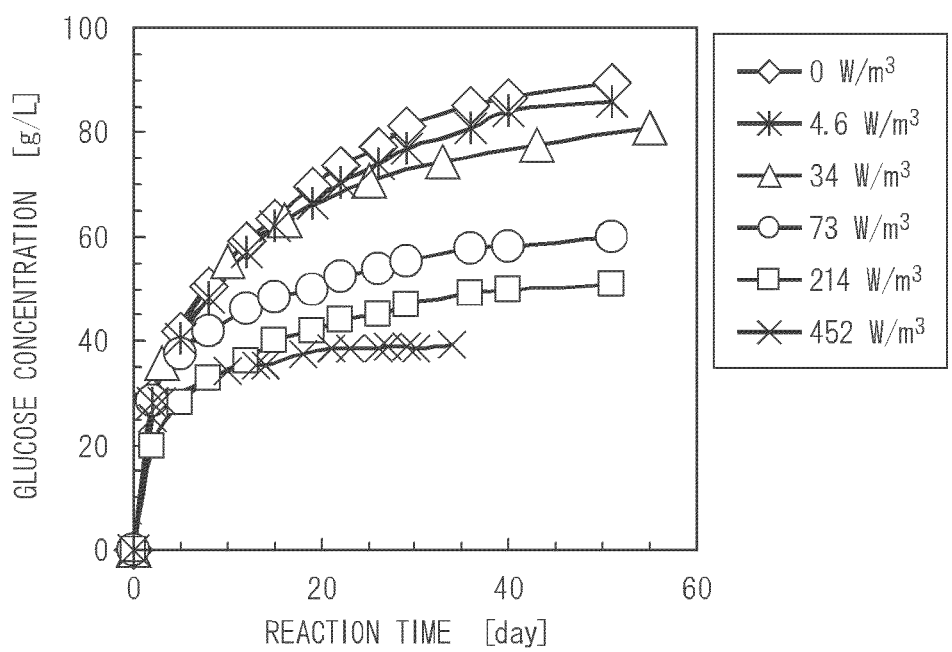
FIG. 2 is a graph showing a relationship between a reaction time (day) and glucose concentration (g/L) in the experimental examples 1 to 6 of the present invention.

The method of producing saccharides containing glucose as the major constituent of the present invention is explained below as an embodiment of the present invention.

Description of this embodiment is for a better understanding of the present invention. Therefore, the descriptions of this embodiment does not particularly limit the present invention as long as being stated it does.

In the method of producing saccharides of the present invention, first, cellulose, hemicellulose, or a mixture of cellulose and hemicellulose is mixed with a enzyme solution to prepare a mixture (slurry). Then, an enzymatic saccharification is performed by saccharifying the cellulose, hemicellulose, or the mixture of cellulose and hemicellulose with a cellulose saccharifying enzyme. In the saccharifying process, the mixture is stirred and mixed in a condition where an energy density Y (W/m$^3$) subjected to the mixture and a substrate concentration X (w/v %), which is a weight (g) of the cellulose, hemicellulose, or the mixture of cellulose or hemicellulose divided by a volume (ml) of the enzyme solution, satisfy a formula (1) below.

$$Y < -0.0125X^2 + 1.195X + 23.25 \qquad (1)$$

Hereinafter, a term "cellulose material" is used for a biomass containing cellulose, hemicellulose, or a mixture of cellulose and hemicellulose.

The Y value (the gross stirring energy density (Wm$^3$)) in the step of saccharifying process is at least more than 0. Assuming a value Z equals to the value of the right side of the formula (1), a preferable Y value ranges from 0.2×Z to 0.9×Z as a practical stand point of view. A more preferable Y value ranges from 0.4×Z to 0.9×Z. Even more preferable Y value ranges from 0.6×Z to 0.9×Z.

In the method of producing saccharides of the present embodiment, a cellulose material and a solution containing a saccharifying enzyme (enzyme solution) enough for degrading the cellulose material are placed in a reaction tank (enzymatic degradation tank). Then, the cellulose material and the enzyme solution are mixed to prepare a mixture (slurry) (step of preparing the mixture).

In this step of preparing the mixture, the pH value of the enzyme solution is adjusted to obtain a pH value suitable for the saccharifying enzyme used. In addition, temperature of the mixture is also adjusted to the temperature suitable for the saccharifying enzyme.

It is preferable to set the pH value of the mixture (slurry) within a range that the enzyme actively performs its catalytic function in this step of preparing the mixture. Specifically, it is preferable to set the pH to 4 to 6.

It is preferable to set temperature of the mixture (slurry) within a range that the enzyme actively performs its catalytic function in this step of preparing the mixture. Specifically, it is preferable that the temperature of the enzyme solution is in the range from 50 to 60° C.

A preferable amount of the cellulose material added to the enzyme solution ranges from 5 to 50 g to 100 mL of the enzyme solution. That means a preferable substrate concentration X ranges from 5 to 50 weight per volume % (w/v %). A more preferable substrate concentration X ranges from 10 to 40 w/v %.

As the cellulose saccharifying enzyme, cellulase is used.

In case where a large amount of hemicellulose is included in the cellulose material, it is preferable to add xylase, mannase, or a mixture of xylase and mannase to the enzyme solution in addition to the cellulase.

As the cellulose material, 1) a processed material obtained by pre-treating a biomass (wood or grass) by delignification process and partial distraction process of the crystal structure of cellulose, 2) a waste material including cellulose as the major constituent obtained from old papers, card board, paper sludges, or the like , 3) cotton fiber waste from shirts or towels, and the like can be used.

The pre-treating of a biomass mentioned above includes an alkaline treatment, an organic solvent treatment, a diluted sulfate treatment, hot water treatment, and the like.

In some cases using the wastes originated from the used paper or the used cotton fiber, the pre-treatment can be omitted.

It is preferable that a residual amount of lignin in the cellulose material after the pre-treatment is 15 wt % or less. The residual amount of lignin in the cellulose material after the pre-treatment is more preferably 5 wt % or less.

The amount of enzyme used can be significantly reduced in the method of producing saccharides of the present embodiment by reducing the residual amount of lignin in the cellulose material within the preferable ranges mentioned above, since the enzyme in the enzyme solution functions more efficiently even if the concentration of the enzyme in the enzyme solution is low (for example, a case in which protein concentration in the enzyme solution is 0.6 g/L or less).

For stirring the mixture (slurry), stirring impellers or the like are used. In the case where the mixture is shaken, a shaker or the like can be used.

In the method of producing saccharides of the present invention, the mixture (slurry) in the reaction tank is mixed gently enough not to cause enzyme deactivation due to physical stress. Therefore, the substrate, which includes cellulose, hemicellulose, or the mixture of cellulose and hemicellulose, can be enzymatically converted to monosaccharide efficiently.

FIG. 1 shows a graph showing a relationship between the substrate concentration in the enzyme solution (w/v %) and the gross maximum stirring energy density (W/m$^3$) that can be subjected to the mixture without causing a significant enzyme deactivation.

The gross maximum stirring energy density (W/m$^3$) means the highest total energy density input to the mixture (slurry) not causing a significant enzyme deactivation in the enzyme solution.

Based on the result shown in FIG. 1, the relationship between the substrate concentration x (w/v %) in the enzyme solution and the gross maximum stirring energy density y (W/m$^3$) that can be subjected to the mixture without causing a significant enzyme deactivation can be expressed by a formula (2) below.

$$y \leq -0.0125x^2 + 1.195x + 23.25 \quad (2)$$

In the method of producing saccharides of the present invention, the gross stirring energy density Y (W/m$^3$) is adjusted not to exceed the value on the right side of the formula (2). Accordingly, mixing of the mixture (slurry) in the enzymatic saccharification process in the method of producing saccharides of the present invention is performed with Y and X values satisfying the formula (1) below.

$$Y \leq -0.0125X^2 + 1.195X + 23.25 \quad (1)$$

By having the Y value being equal to or less the value on the right side of the formula (1), enzymatic saccharification proceeds efficiently without enzyme deactivation.

When the gross stirring energy density Y (W/m$^3$) exceeds the value on the right side of the formula (2), which is the gross maximum stirring energy density y (W/m$^3$) that can be subjected to the mixture without causing a significant enzyme deactivation, excess physical stress is placed on the enzymes. As a result, the saccharifying enzymes are deactivated, reducing the saccharification performance. On the other hand, there is no specific lower limit for the Y value, since the deactivation of the enzyme can be avoided as long as the X and Y values satisfy the formula (1).

It is preferable to control the temperature of the mixture (slurry) allowing the enzyme to function actively. Specifically, it is preferable to control the temperature of the mixture (slurry) between 50 to 60° C.

The step of the enzymatic saccharification can be prolonged until the saccharification proceeds sufficiently without further progress of the reaction. For example, the step of the enzymatic saccharification can be performed for 2 to 60 days at 50 to 60° C.

A probable reason why the enzymatic saccharification proceeds efficiently when the mixture (slurry) is gently mixed in a condition where the concentration of the enzyme is low (protein concentration in the enzyme solution is 0.6 g/L or less), is explained below.

In conventional method of producing saccharides from a cellulosic biomass, the mixture (slurry) is mixed too vigorously for a condition with low enzyme concentration (protein concentration in the enzyme solution is 0.6 g/L or less). As a result, a significant amount of the saccharifying enzymes lose their activity, making it impossible to obtain efficient saccharification with a small amount of the enzyme.

In the method of producing saccharides of the present invention, the enzyme deactivation caused by the vigorous mixing can be suppressed by gently mixing the mixture (slurry) containing the cellulose material and the enzyme solution. Consequently, the enzyme in the enzyme solution can function efficiently. Therefore, sugar production can be significantly improved even with a small amount of the saccharifying enzyme. In addition, temperature and constituents in the reaction tank can be evenly distributed by the gentle mixing. As a result, the enzymatic saccharification can be more efficient even in a larger reaction apparatus.

The method of producing saccharides of the present invention is explained in detail with examples below. However, the method of producing saccharides of the present invention is not particularly limited by the descriptions of the examples.

EXAMPLE 1

One liter of 50 mM acetate buffer (pH 5.0) including 5 ml of a cellulase solution was placed in a cylindrically-shaped reaction tank with an inner diameter of 130 mm and a height of 300 mm. As a cellulose material, 100 g of a filter paper was immersed in the enzyme solution. The ratio of cellulase protein to the weight of the filter paper was 6 mg/g (protein mg/filter paper g).

The filter paper concentration in the enzyme solution x was 10 w/v %, since the weight of the filter paper was 100 g and the volume of the enzyme solution was 1 L (1000 mL).

The enzyme solution having the filter paper submerged (the mixture) was incubated at 50° C. undisturbed without stirring or shaking (energy density is 0 W/m$^3$) to allow the enzymatic saccharification to proceed. Then, relationship between the reaction time and the glucose concentration was monitored and plotted.

Figure 3:
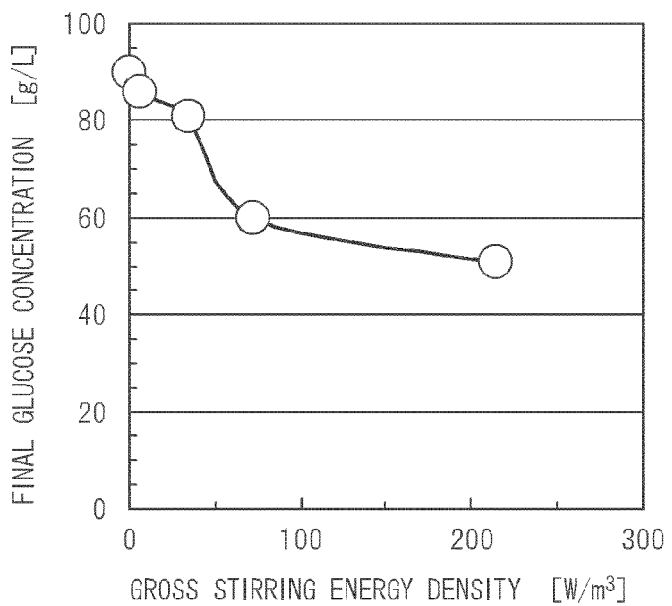
FIG. 3 is a graph showing a relationship between a stirring energy density (W/m$^3$) and the final glucose concentration (g/L) in the experiment examples 1 to 6 of the present invention.
Figure 4:
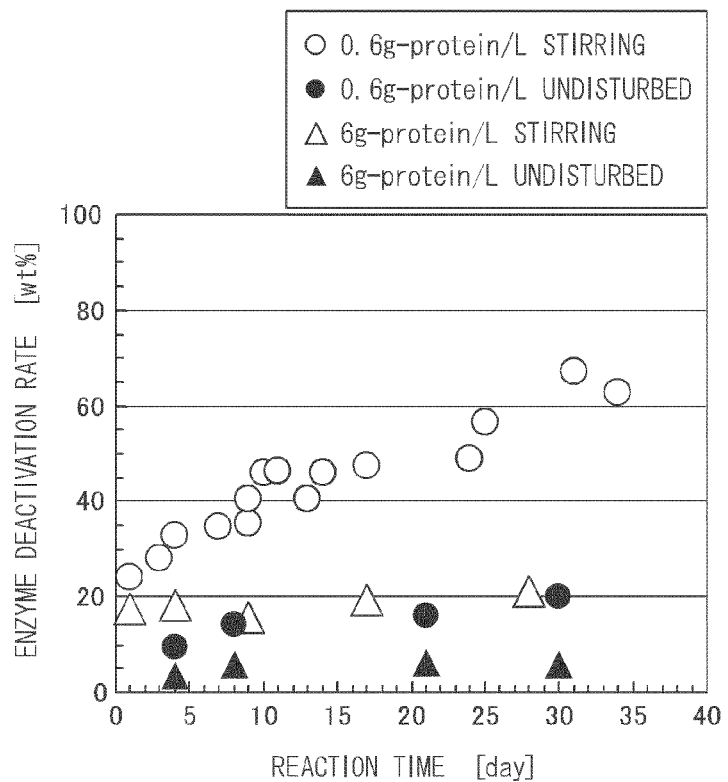
FIG. 4 is a graph showing a relationship between stirring time (day) and the amount of enzyme deactivation (wt %).

A relationship between the gross stirring energy density and the final glucose concentration in Example 1 was plotted on a graph shown in FIG. 3.

EXAMPLE 2

A mixture was prepared as described in Example 1. In Example 2, the enzymatic saccharification was performed in a condition where the mixture was stirred with a stirring energy density of 4.6 W/m$^3$ at 50° C.

As in Example 1, a relationship between the reaction time and the glucose concentration was monitored and plotted.

A relationship between the gross stirring energy density and the final glucose concentration in Example 2 was also plotted on a graph shown in FIG. 3.

In Example 2, the enzymatic saccharification was performed in a condition where the X and Y values satisfied the formula (1), since the X value was 10 and the Y value was 4.6 (W/m³). When the X value was 10, the value on the right side of the formula (1) is 33.95.

EXAMPLE 3

A mixture was prepared as described in Example 1. In Example 3, the enzymatic saccharification was performed in a condition where the mixture was stirred with a stirring energy density of 34 W/m³ using stirring impellers at 50° C.

As in Example 1, a relationship between the reaction time and the glucose concentration was monitored and plotted.

A relationship between the gross stirring energy density and the final glucose concentration in Example 3 was also plotted on a graph shown in FIG. 3.

EXAMPLE 4

A mixture was prepared as described in Example 1. In Example 4, the enzymatic saccharification was performed in a condition where the mixture was stirred with a stirring energy density of 73 W/m³ using stirring impellers at 50° C.

As in Example 1, a relationship between the reaction time and the glucose concentration was monitored and plotted.

A relationship between the gross stirring energy density and the final glucose concentration in Example 4 was also plotted on a graph shown in FIG. 3.

The enzymatic saccharification was performed in a condition where the X and Y values did not satisfy the formula (1) in Example 4, since the X value was 10 and the Y value was 73 (W/m³).

EXAMPLE 5

A mixture was prepared as described in Example 1. In Example 5, the enzymatic saccharification was performed in a condition where the mixture was stirred with a stirring energy density of 214 W/m³ using stirring impellers at 50° C.

As in Example 1, a relationship between the reaction time and the glucose concentration was monitored and plotted.

A relationship between the gross stirring energy density and the final glucose concentration in Example 5 was also plotted on a graph shown in FIG. 3.

The enzymatic saccharification was performed in a condition where the X and Y values did not satisfy the formula (1) in Example 5, since the X value was 10 and the Y value was 214 (W/m³).

EXAMPLE 6

A mixture was prepared as described in Example 1. In Example 6, the enzymatic saccharification was performed in a condition where the mixture was stirred with a stirring energy density of 452 W/m³ using stirring impellers at 50° C.

As in Example 1, a relationship between the reaction time and the glucose concentration was monitored and plotted.

A relationship between the gross stirring energy density and the final glucose concentration in Example 6 was also plotted on a graph shown in FIG. 3.

The enzymatic saccharification was performed in a condition where the X and Y values did not satisfy the formula (1) in Example 6, since the X value was 10 and the Y value was 452 (W/m³).

It was demonstrated that the final glucose concentration was significantly reduced when the gross stirring energy density was 73 W/m³ or higher, while there was no or only slight decrease of the final glucose concentration when the gross stirring energy density was 34 W/m³ or lower. These results indicate that the enzymatic saccharification was inhibited by the strong stirring energy density, when it was 73 W/m³ or higher. It seems that a fraction of the enzymes was deactivated by the strong stirring energy density.

When the final glucose concentrations were compared between the reactions mixed with the gross stirring energy density of 34 W/m³ or less, and the reaction mixed with the energy density of 73 W/m³, there was a significant decrease in the latter case. Thus, it was shown that there is a threshold value between 34 and 73 W/m³. When the stirring energy density exceeds the value, the enzymes lose their activity rapidly.

When the final glucose concentrations were compared between the reaction mixed with the gross stirring energy density of 73 W/m³ and that of 214 W/m³, there was no significant difference observed. From this result, it was suggested that once the stirring energy density exceeds the threshold, enzyme deactivation proceeds rapidly and the effect the gross stirring energy density to the final glucose concentration becomes negligible.

Based on the results explained above, it was shown that when the concentration of the saccharifying enzyme is low (protein concentration is 0.6 g/L or less), the gross stirring energy density input to the mixture (slurry) is needed to be 34 W/m³ or less in order to maintain an effective enzymatic saccharification in the case where the mixture (slurry) containing the enzyme solution and the filter paper.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A method of producing saccharides containing glucose as the major constituent, comprising the steps of:
providing, in a reaction tank:
a pre-treated biomass substrate, which contains
at least one selected from the group consisting of cellulose and hemicellulose, and
lignin; and
a solution, which includes a cellulose saccharifying enzyme;
combining the substrate with the solution to prepare a mixture;
after the step of combining, saccharifying in the reaction tank for 2 to 60 days at a temperature in the range from 50° C. to 60° C. the at least one selected from the group consisting of cellulose and hemicellulose with the cellulose saccharifying enzyme;
providing stirring impellers in the reaction tank; and
during the step of saccharifying, agitating the mixture with said stirring impellers at an agitation power Y (W/m³) determined based on a substrate concentration X (w/v %) using a formula (1) below, $$Y \leq -0.0125X^2 + 1.195X + 23.25 \tag{1}$$

wherein the substrate concentration X (w/v %) is a value obtained by dividing a mass (g) of the at least one selected from the group consisting of cellulose and hemicellulose by a volume (mL) of the solution and multiplying by 100, Y is at least more than zero and X ranges from 5 to 50 w/v %, an amount of the lignin in the substrate is 15 wt % or less, a pH value of the mixture is 4 to 6, and protein concentration in the solution is 0.6 g/L or less.

2. A method of producing saccharides containing glucose as the major constituent, comprising the steps of:

providing, in a reaction tank:
- a pre-treated biomass substrate, which contains
  - at least one selected from the group consisting of cellulose and hemicellulose, and
  - lignin, and
- a solution, which includes a cellulose saccharifying enzyme;

combining the substrate with the solution to prepare a mixture;

after the step of combining, saccharifying in the reaction tank for 2 to 60 days at a temperature in the range from 50° C. to 60° C. the at least one selected from the group consisting of cellulose and hemicellulose with the cellulose saccharifying enzyme;

providing a shaker supporting the reaction tank; and during the step of saccharifying, agitating the mixture with said shaker at an agitation power Y (W/m$^3$) determined based on a substrate concentration X (w/v %) using a formula (1) below, $$Y \leq -0.0125X^2 + 1.195X + 23.25 \qquad (1)$$

wherein the substrate concentration X (w/v %) is a value obtained by dividing a mass (g) of the at least one selected from the group consisting of cellulose and hemicellulose by a volume (mL) of the solution and multiplying by 100, Y is at least more than zero and X ranges from 5 to 50 w/v % an amount of the lignin in the substrate is 15 wt % or less, a pH value of the mixture is 4 to 6, and protein concentration in the solution is 0.6 g/L or less.

* * * * *